United States Patent [19]

O'Neill

[11] Patent Number: 5,185,474

[45] Date of Patent: Feb. 9, 1993

[54] SYNTHESIS OF FLUORINATED DIMETHYL ETHERS

[75] Inventor: Gerald J. O'Neill, Arlington, Mass.

[73] Assignee: W. R. Grace & Co.-Conn., Lexington, Mass.

[21] Appl. No.: 875,553

[22] Filed: Apr. 27, 1992

Related U.S. Application Data

[63] Continuation of Ser. No. 591,578, Oct. 2, 1990, abandoned.

[51] Int. Cl.$^5$ ............................................. C07C 41/22
[52] U.S. Cl. ............................... 568/684; 204/157.92; 204/157.94; 568/683
[58] Field of Search ................................ 568/683, 684; 204/157.92, 157.94

[56] References Cited

U.S. PATENT DOCUMENTS

| | | | |
|---|---|---|---|
| 2,066,905 | 1/1937 | Booth | 260/151 |
| 2,533,132 | 12/1950 | McBee | 260/653 |
| 3,461,213 | 8/1969 | Terrell | 568/684 |
| 3,663,715 | 5/1972 | Terrell | 568/684 |
| 3,689,459 | 9/1972 | Reagan | 260/614 F |
| 3,806,602 | 4/1974 | Croix | 424/342 |
| 3,879,474 | 4/1975 | Croix | 260/614 F |
| 3,887,439 | 6/1975 | Hutchinson | 203/63 |
| 3,897,502 | 7/1975 | Russell et al. | 260/614 F |
| 4,023,567 | 5/1977 | Hutchinson et al. | 260/616 |
| 4,113,435 | 9/1978 | Lagow et al. | 422/191 |
| 4,149,018 | 4/1979 | Bell et al. | 568/684 |
| 4,874,901 | 10/1989 | Halpern et al. | 568/683 |
| 4,961,321 | 10/1990 | O'Neill et al. | 62/114 |

OTHER PUBLICATIONS

Chemical Abstract, vol. 52,44676 (1958); "Methylene Derivatives as Intermediates in Polar Reactions", *Journal of the American Chemical Society*, 79, 5493–6 (1957).
Chemical Abstract, vol. 55,12270 (1961).
Chemical Abstract, vol. 55,23312 (b) (1961).
Chemical Abstract, vol. 55,27012 (i) (1961).
Chemical Abstract, vol. 56,9938 (c) (1962).
Chemical Abstract, vol. 82,43287 (j) (1975).

*Primary Examiner*—Howard T. Mars
*Assistant Examiner*—Kimberly J. Kestler
*Attorney, Agent, or Firm*—John Dana Hubbard; William L. Baker

[57] ABSTRACT

A novel process is disclosed for the synthesis of fluorinated dimethyl ethers of the formula $CF_2HOCCl_XF_YH_{3-(X+Y)}$ wherein X and Y are each independently 0, 1, 2 or 3 and wherein the total X+Y is 2 or 3. The process involves chlorination of methyl difluoromethyl ether to form a chlorinated reaction product, including at least one compound of the formula $CF_2HOCH_{3-z}Cl_z$, wherein z is 1, 2 or 3, which compound is then fluorinated, with or without separation from the chlorinated reaction product, to give a fluorinated reaction product including the aforementioned fluorinated dimethyl ethers.

5 Claims, No Drawings

SYNTHESIS OF FLUORINATED DIMETHYL ETHERS

This is a continuation of application Ser. No. 591,578, filed on Oct. 2, 1990, now abandoned.

BACKGROUND OF THE INVENTION

Field of the Invention

This invention relates to a process for the synthesis of fluorinated dimethyl ethers which have utility as refrigerants, as blowing agents, etc.

Bis(difluoromethyl)ether has been prepared previously by chlorination of dimethyl ether followed by isolation and fluorination of bis(dichloromethyl)ether. The chlorination step gave a complex mixture of chlorinated dimethyl ethers some of which were unstable, e.g. to distillation, from which bis(dichloromethyl)ether was separated. Two of the ethers in the mixture, chloromethyl methyl ether and bis-(chloromethyl)ether, are potent carcinogens.

SUMMARY OF THE INVENTION

Accordingly, it is an object of the present invention to provide a process for synthesis of fluorinated dimethyl ethers which does not produce carcinogens as intermediates.

Another object of the present invention is to provide a process for synthesis of fluorinated dimethyl ethers wherein the various required separations may be effected by distillation without lost of yield and danger of explosion due to marked instability of the various intermediates.

The unstable complex mixture of chlorinated ethers, some of which are carcinogens, in accordance with the prior art, is avoided in the present invention by employing methyl difluoromethyl ether as a starting material. The methyl difluoromethyl ether is chlorinated to give a chlorinated reaction mixture including at least one compound of the formula $CF_2HOCH_{3-z}C_z$, wherein z is 1, 2 or 3, which compound can readily be separated from the chlorinated reaction mixture. The chlorination of methyldifluoromethyl ether can form only three derivatives, i.e. z=1, z=2 and z=3. The dichloromethyl difluoromethyl ether (z=2) can readily be separated from the chlorinated reaction mixture and is then fluorinated, with or without such separation, to form the bis(difluoromethyl)ether. $CF_2HOCCl_3$ (z=3) may also be separated from the chlorination reaction product and fluorinated. Alternatively, the chlorination reaction product itself may be fluorinated (without prior separation) as follows:

$$CF_2HOCH_2Cl \longrightarrow CF_2HOCH_2F \quad (I)$$

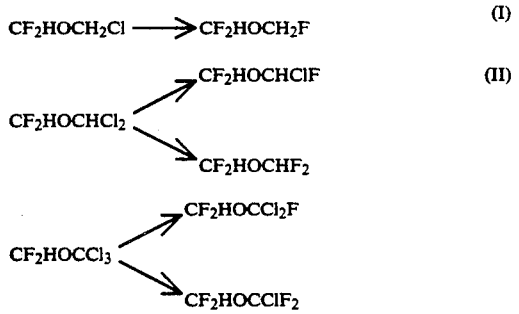

(II)

All of the above would find utility as refrigerants, especially (I) monofluoromethyl difluoromethyl ether and (II) bis(difluoromethyl)ether, which are considered to be sustitutes for R-11 and R-114 refrigerants, respectively.

The chlorination and fluorination steps of the present invention may be represented as follows:

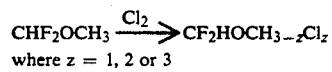

where z = 1, 2 or 3

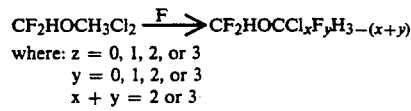

where: z = 0, 1, 2, or 3
y = 0, 1, 2, or 3
x + y = 2 or 3

DESCRIPTION OF THE PREFERRED EMBODIMENTS

The methyl difluoromethyl ether which is regarded as the starting material for the process of the present invention is a known compound which may be prepared in the manner reported by Hine and Porter in their article published in the *Journal of the American Chemical Society*. See "Methylene derivatives as intermediates in polar reactions. VIII. Difluoromethylene in the reaction of chlorodifluoromethane with sodium methoxide." Jack Hine and John J. Porter, *J. Am. Chem. Soc.* 79, 5493–6(1957), the teachings of which are incorporated herein by reference. In their article Hine and Porter describe the production of difluoromethyl methyl ether ($CH_3OCHF_3$) by reaction of sodium methoxide NaOMe with chlorodifluoromethane ($ClF_3CH$), which reaction may be represented as follows:

Briefly, the method involves forming an alcohol solution of sodium methoxide and bubbling the chlorodifluoromethane slowly through the reaction mixture to obtain the methyldifluoromethyl ether as a residue in the reaction mixture.

The starting ether, $CF_2OCH_2$, might also be prepared by first reacting NaOH with $CH_3OH$, in effect making $CH_3ONa$, and then reacting it with $CF_2HCl$. However, water is also formed in the $NaOH/CH_3OH$ reaction and the effect the water would have on the subsequent reaction to form $CF_2HOCH_3$ is presently unknown.

In accordance with the present invention, methyldifluoromethyl ether is chlorinated as follows:

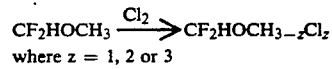

where z = 1, 2 or 3

It has been found that the $CF_2HOCH_3$ may suitably be chlorinated by liquefying the $CF_2HOCH_3$ and reacting it with chlorine gas while irradiating with a source of visible light. The chlorination of $CF_2HOCH_3$ can form only three derivatives, from which $CF_2HOCHCl_2$ and/or $CF_2HOCCl_3$ can be readily separated prior to fluorination or the reaction mixture can be fluorinated without separation to give an admixture of $CF_2HOCFCl_2$, $CF_2HOCF_2Cl$ $CF_2HOCH_2F$, $CF_2HOCFHCl$ and $CF_2HOCF_3H$. All separations may be effected by fractional distillation.

One method found suitable for the fluorination of the chlorination reaction product involves reaction of the halogenated dimethylether or ethers with antimony trifluoride. The reaction may be represented as follows:

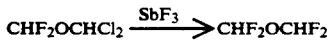

On an industrial scale the antimony trifluoride reacation can be carried out in a continuous mode by a continuous regeneration of the catalyst with HF. This is done by using a mixture of $SbF_3$ and chlorine to give the pentavalent salt $SbF_3Cl_2$, or on a small scale it can be done by using a mixture of $SbF_3$ and $SbCl_5$, as in example 2 which follows. More commonly, antimony pentachloride alone is used as follows:

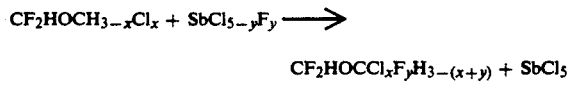

The mixed salt catalyst, likewise, may be continuously regenerated by the addition of HF.

In an alternative fluorination procedure the chlorinated reaction product is reacted with anhydrous hydrogen fluoride (HF), which reaction may be represented as follows:

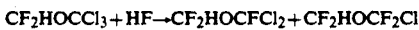

Utilizing the above reaction with hydrogen fluoride the present inventor has obtained a yield as high as 78% $CF_2HOCF_2Cl$ with a small amount of $CF_2HOCFCl_2$. This was an unexpected result since HF does not normally replace a halogen such as chlorine, except perhaps at very high temperatures, but instead fluorinates by continuous regeneration of a fluorinating agent such as $SbF_2$ or $SbF_3Cl_2$. Apparently, the difluoromethoxy group activates the chlorine on the alpha-carbon atom allowing it to react readily with HF.

The present invention will now be further illustrated by the following examples.

EXAMPLE 1 a) Preparation of $CF_2HOCH_3$

Methanol (1000 mls) was placed in a three-liter, three-necked, round-bottomed flask fitted with a magnetic stirrer, thermometer, gas dispersion tube, condenser cooled to $-78°$ C. and connected to a trap also cooled to $-78°$ C. Sodium methoxide (2215 g) was added slowly while stirring the mixture. The temperature of the reaction flask was adjusted to 45–55° C. and maintained in that range during the reaction. Chlorodifluoromethane (569 g) was bubbled slowly through the reaction mixture over a period of 6¼ hours. The material recovered from the trap was warmed to $-26°$ C. for about 15 minutes to remove excess $CHF_2Cl$. The weight of residual material was 250.6 g. GC analysis of the residue showed it to contain 85.4% $CF_2HOCH_3$, a 65% yield, based on $CH_3ONa$.

b) Chlorination of $CF_2HOCH_3$

Apparatus consisted of a three-necked, 250-ml round-bottomed flask fitted with a thermometer, a gas dispersion tube, an air condenser connected in series with a dewar condenser, a cold trap $(-78°$ C.) and a HCl scrubber.

The dewar condenser was cooled to about $-30°$ C. with dry ice/methanol and the reaction flask cooled in a similar fashion to $-15°$ C. The apparatus was flushed with nitrogen for 15 minutes to remove oxygen. A mixture of $CF_2HOCH_3$ and $CHF_2Cl$ (total weight 125.9 g and containing 65% $CF_2HOCH_3$), as obtained from the preparation in section (a), was condensed into the flask and chlorine gas (140 g) added over a period of 1¾ hour while irradiating the flask with a 300-watt sunlamp. The material recovered from the cold trap (76 g) contained 90.5% $CF_2HOCHCl_2$, a yield of 37%.

c) fluorination of $CHF_2OCHCl_2$

Antimony trifluoride (9.8 g) and $CF_2HOCHCl_2$ (24.9 g) were placed in 50 ml 3-necked round-bottomed flask fitted with a thermometer, a magnetic stirrer and a water condenser connected in series with a cold trap. The mixture was stirred for ¼ hour then heated to 57° C. for 15 minutes.

GC analysis of the material recovered from the cold trap showed it to contain 64.2% $CHF_2OCHF_2$, a yield of 62.5%. The other product of the reaction, $CHF_2OCHFCl_2$ accounted for 26.5% of the product mixture.

EXAMPLE 2

$CF_2HOCH_3$, (166 g), was chlorinated, as in Example 1 section (b), to give 98.8 g of product containing 9.4% $CHF_2OClH_2$, 29.1% $CF_2HOCHCl_2$ and 51.1% $CHF_2OCCl_3$. A portion (13.6 g) of this mixture was then fluorinated in an apparatus similar to that described in section (c) of Example 1. $SbF_3$ (7.4 g) and $SbCl$ (0.75 g) were placed in the reaction flask and the chlorinated product slowly added to the stirred mixture. The temperature of the reaction system rose to 44° C. without the application of heat. GC analysis of the recovered product (9.2 g) showed it to consist of $CF_2HOCF_2H$ (27.0%), $CF_2HOCF_3Cl$ (38.4%) and $CF_2HOCFCl_2$ (21.89%).

EXAMPLE 3 alternative fluorination step

A sample of chlorinated difluoromethyl ether mixture (25 gm) containing 50% $CF_2HOCCl_3$, was placed in a polyethylene flask fitted with an inlet tube for nitrogen as carrier gas, an outlet tube leading to a second polyethylene flask containing NaOH solution (10%), followed by a drying tube and a trap cooled in Dry Ice/MeOH.

An excess of anhydrous hydrogen fluoride was added to the chlorinated ether and the mixture stirred with a magnetic stirrer. Heat was not applied, the temperature remaining at about 20° C. More hydrogen fluoride was added to the mixture as needed until all the organic material had reacted. The weight of material collected from the cold trap was 9.5 g.

Analysis of the recovered product by GC showed it to consist of 84.3% $CF_2HOCF_2Cl$, a yield of 78% based on the $CF_2HOCCl_3$ content of the chlorinated mixture. A small amount of $CF_2HOCFCl_2$ was also present.

The invention ma be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A process for the preparation of fluorinated dimethyl ethers of the formula $CF_2HOCCl_xF_yH_{3-(x+y)}$, wherein x is 0, 1, or 2 and y is 1, 2, or 3 and wherein the total $x+y$ is 1, 2 or 3, said process consisting essentially of:

chlorinating $CF_2HOCH_3$ in a liquid phase by reacting said $CF_2HOCH_3$ with chlorine gas n the presence of light to form a chlorinated admixture containing at least one compound of the formula $CF_2HOCH_{3-z}Cl_z$ wherein z is 1, 2 or 3; and flourinating said at least one compound of the formula $CF_2HOCH_{3-z}Cl_z$ with anhydrous HF in the absence of a catalyst to obtain a fluorinated admixture containing at least one compound of a formula $CF_2HOCl_yF_zH_{3-(y+z)}$ wherein y is 0, 1 or 2 and z is 1, 2 or 3.

2. A process in accordance with claim 1 wherein said one compound of the formula $CF_2HOH_{3-z}Cl_2$ and said fluorinated admixture includes $CF_2HOCF_2H$, $CF_2HOCFCl_2$ and $CF_2HOCF_2Cl$.

3. A process in accordance with claim 1 wherein said one compound of the formula $CF_2HOCH_{3-z}Cl_2$ is $CHF_2OCHCl_2$ and said one compound of the formula $CF_2HOCCl_xF_yH_{3-(x+y)}$ is $CHF_2OCHF_2$ and further comprising separating and recovering said $CHF_2OCHF_2$ from said fluorinated admixture.

4. A method in accordance with claim 1 wherein said one compound of the formula $CF_2HOCH_{3-z}Cl_2$ is $CF_2HOCCl_3$ and said one compound of the formula $CF_2HOCCl_xF_yH_{3-(x+y)}$ is $CF_2HOCF_2Cl$ and further comprising separating and recovering said $CF_2HOCF_2Cl$ from solution.

5. A method in accordance with claim 1 additionally comprising reacting $CHF_2Cl$ with an alkali metal methoxide in solvent solution to form said $CHF_2OCH_3$.